(12) United States Patent
Costantino et al.

(10) Patent No.: US 8,227,596 B2
(45) Date of Patent: *Jul. 24, 2012

(54) PROCESS FOR THE PREPARATION OF DROSPIRENONE

(75) Inventors: Francesca Costantino, Milan (IT); Roberto Lenna, S. Giorgio Su Legnano (IT); Silvia Piuri, Saronno (IT)

(73) Assignee: Industriale Chimica S.R.L., Milan (IT)

( * ) Notice: Subject to any disclaimer, the term of this patent is extended or adjusted under 35 U.S.C. 154(b) by 31 days.

This patent is subject to a terminal disclaimer.

(21) Appl. No.: 12/850,246

(22) Filed: Aug. 4, 2010

(65) Prior Publication Data

US 2010/0331291 A1    Dec. 30, 2010

Related U.S. Application Data

(63) Continuation of application No. 11/792,465, filed as application No. PCT/EP2005/055963 on Nov. 14, 2005.

(30) Foreign Application Priority Data

Dec. 6, 2004  (IT) .............................. MI2004A2338

(51) Int. Cl.
*C07J 53/00* (2006.01)
(52) U.S. Cl. ........................................................ 540/15
(58) Field of Classification Search ..................... 540/15
See application file for complete search history.

(56) References Cited

U.S. PATENT DOCUMENTS 6,121,465 A * 9/2000 Mohr et al. ................... 549/265

OTHER PUBLICATIONS

Arjan E.J. de Nooy et al.; "On the Use of Stable Organic Nitroxyl Radicals for the Oxidation of Primary and Secondary Alcohols"; Synthesis, Oct. 1996, pp. 1153-1174.
Bruckner C. et al.; "Preparation of Tetramethylpiperidine-I-Oxoammonium Salts and their Use as Oxidants in Organic Chemistry. A Review." Organic Preparation and Procedures Int., 36 (1), 3-31, 2004.
Decision dated Jan. 4, 2012 in Seilz v. Costantino; Patent Interference No. 105,788 (MPT).
Judgment dated Jan. 4, 2012 in Seilz v. Costantino; Patent Interference No. 105,788 (MPT).
Decision dated Mar. 28, 2012 in Seilz v. Costantino; Patent Interference No. 105,788 (MPT).
Inokuchi et al; Recent Advances in the Catalytic Oxidation of Alcohols with 2,2,6,6-Tetramethylpiperidine-1-oxyl (TEMPO) and Its Application to Organic Synthesis; 1993; vol. 51; No. 10; 48-58. (Abstract).
Serra et al.; Natural p-Menthene Monoterpenes: Synthesis of the Enantiomeric Forms of Wine Lactone, Epi-wine Lactone, Dill Ether, and Epi-dill Ether Starting from a Common InTermediate; Helevetica Chimica Acta, 2004; vol. 87; 2100-2109.

* cited by examiner

*Primary Examiner* — Nizal Chandrakumar
(74) *Attorney, Agent, or Firm* — Abelman, Frayne & Schwab

(57) ABSTRACT

A process is described for the preparation of drospirenone, a synthetic steroid with progestogenic, antimineralocorticoid and antiandrogenic activity, useful for preparing pharmaceutical compositions with contraceptive action by the oxidation of 17α-(3-hydroxypropyl)-6β,7β,15β,16β-dimethylene-5β-androstane-3β,5,17β-triol.

25 Claims, No Drawings

PROCESS FOR THE PREPARATION OF DROSPIRENONE

This application is a continuation of U.S. Application Ser. No. 11/792,465, filed Jun. 4, 2007, which is a National Phase of PCT/EP2005/055963, filed 14 Nov. 2005, which claims priority from Italian Application Ser. No. MI2004A002338. filed 6 Dec. 2004.

FIELD OF THE INVENTION

The present invention relates to the field of processes for synthesising steroids, and in particular to a process for the industrial scale preparation of drospirenone.

STATE OF THE ART

The compound of formula (I) given hereinafter, whose chemical name is 6β,7β; 15β,16β-dimethylene-3-oxo-17α-pregn-4-ene-21,17-carbolactone, is commonly known as drospirenone:

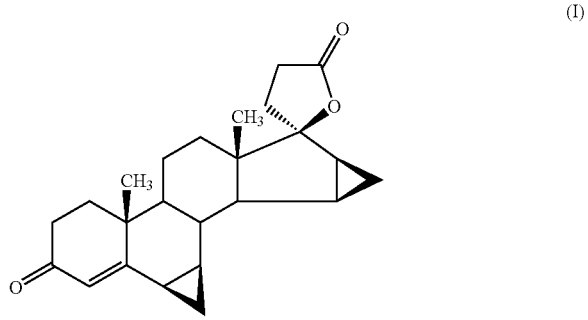

(I)

It is a synthetic steroid with progestogenic, antimineralocorticoid and antiandrogenic activity; by virtue of these characteristics drospirenone has long been used for preparing pharmaceutical compositions with contraceptive action for oral administration.

Many processes are known in the literature for preparing drospirenone, for example the process described in European Patent No. 0 075 189, starting from 3β,7α,15α-trihydroxy-5-androsten-17-one passing via the intermediate 5,6β-epoxy-7β-hydroxy-15β,16β-methylene-3β-pivaloyloxy-5β-androstan-17-one.

As described in EP 0 075 189, this intermediate is then transformed into 7α-chloro-5,6β-epoxy-15β,16β-methylene-3β-pivaloyloxy-5β-androstan-17-one by a reaction that uses tetrachloromethane both as reagent and reaction solvent. The use of this highly toxic solvent in relatively large quantities is one of the unfavourable aspects of this process.

In the process described in EP 0 075 189 the intermediate 17α-(3-hydroxypropyl)-6β,7β; 15β,16β-dimethylene-5β-androstane-3β,5,17β-triol is arrived at from the intermediate 7α-chloro-5,6β-epoxy-15β,16β-methylene-3β-pivaloyloxy-5β-androstan-17-one by way of several steps, from which the final product drospirenone is obtained by oxidising with a pyridine/water/chromic anhydride mixture under hot conditions. This step constitutes a further disadvantage of the known process: chromic anhydride, as all Cr (VI) compounds, is actually a known carcinogen whose use is subject to legislative restrictions such that the precautions required during the use and disposal of these products render them practically unusable.

Another process for preparing drospirenone is described in European Patent No. 0 918 791 B8 wherein the drospirenone is produced in two distinct phases starting from 17α-(3-hydroxypropyl)-6β,7β,15β,16β-dimethylene-5β-androstane-3β,5,17β-triol, using a ruthenium salt as oxidant; in the examples given in said patent crude drospirenone is obtained with a chromatographic purity of 93% which is then improved by chromatography.

At this point it is worth noting that a possible technique is the systematic chromatographic purification of industrial batches of steroids, requiring however dedicated equipment and working environments and consequently a considerable logistic and economic involvement.

There is therefore still a need for a process which enables high purity drospirenone to be prepared, but without presenting the aforestated disadvantages of processes of the known art.

SUMMARY OF THE INVENTION

The Applicant has now developed a process that enables drospirenone with a high degree of purity to be obtained, suitable for use in the preparation of pharmaceutical compositions, and which overcomes the aforestated disadvantages connected to the use of toxic and carcinogenic reagents and the need for chromatographic purifications of crude drospirenone to obtain a high final purity.

Subject of the present invention is therefore a process for the preparation of drospirenone, comprising the oxidation of 17α-(3-hydroxypropyl)-6β,7β,15β,16β-dimethylene-5β-androstane-3β,5,17β-triol of formula (VIII) with a suitable oxidising agent in an organic solvent in the presence of a catalytic amount of 2,2,6,6-tetramethylpiperidine-1-oxyl radical or a derivative thereof, said oxidation being followed by the addition of a protic acid directly into the same reactor in which the oxidation took place, to obtain the drospirenone of formula (I)

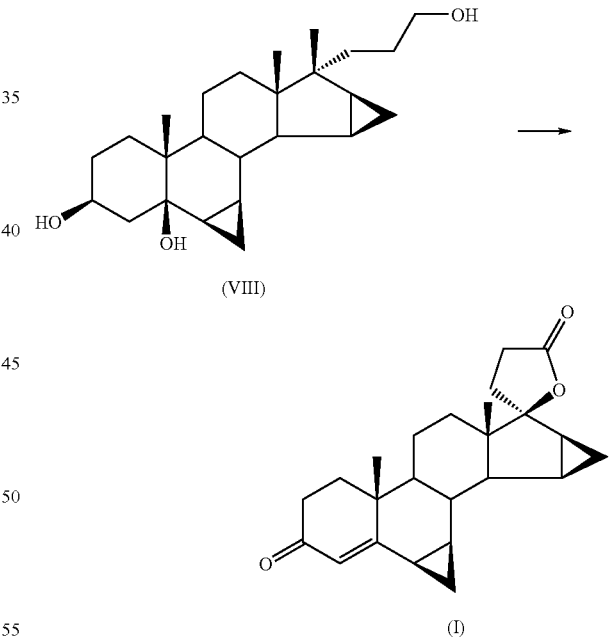

Further subject of the invention is drospirenone obtained by the above said process, and a pharmaceutical composition comprising the drospirenone obtained by the above said process as active principle, and a carrier.

The characteristics and advantages of the present process will be illustrated in detail in the description which follows.

DETAILED DESCRIPTION OF THE INVENTION

The oxidation substrate of the present process, i.e. 17α-(3-hydroxypropyl)-6β,7β,15β,16β-dimethylene-5β-androstane-3β,5,17β-triol, can be obtained starting from commercial products by procedures known to any expert of the art. Preferably this product is obtained from 5,6β-epoxy-7β-hydroxy-15β,16β-methylene-3β-pivaloyloxy-5β-androstan-17-one, in accordance with the procedure comprising the following steps:

a) bromination in position 7α of 5,6β-epoxy-7β-hydroxy-15β,16β-methylene-3β-pivaloyloxy-5β-androstan-17-one of formula (II) to obtain 7α-bromo-5,6β-epoxy-15β,16β-methylene-3β-pivaloyloxy-5β-androstan-17-one of formula (III) by reacting the compound of formula (II) with mesyl chloride to obtain the corresponding mesylate which is not isolated and from which the compound of formula (III) is obtained by the addition of lithium bromide:

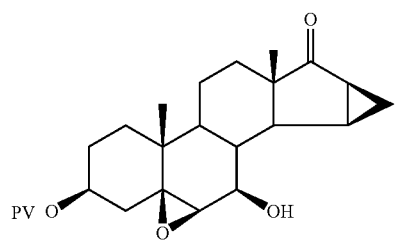

(II)

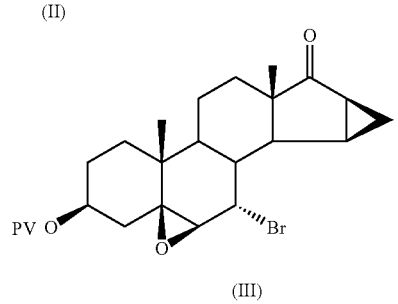

(III)

in which the symbol PV indicates a pivaloyl group, i.e. a trimethylacetyl group;

b) opening the epoxy ring and removing the bromine from 7α-bromo-5,6β-epoxy-15β,16β-methylene-3β-pivaloyloxy-5β-androstan-17-one of formula (III) coming from step a) to obtain 5-hydroxy-15β,16β-methylene-3β-pivaloyloxy-5β-androst-6-en-17-one of formula (IV):

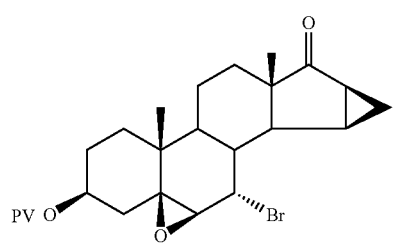

(III)

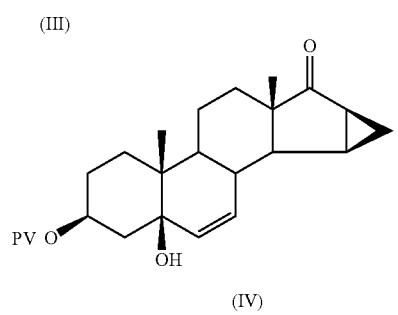

(IV)

c) hydrolysis of the pivaloyl group of 5-hydroxy-15β,16β-methylene-3β-pivaloyloxy-5β-androst-6-en-17-one of formula (IV) coming from step b) to obtain 3β,5-dihydroxy-15β,16β-methylene-5β-androst-6-en-17-one of formula (V):

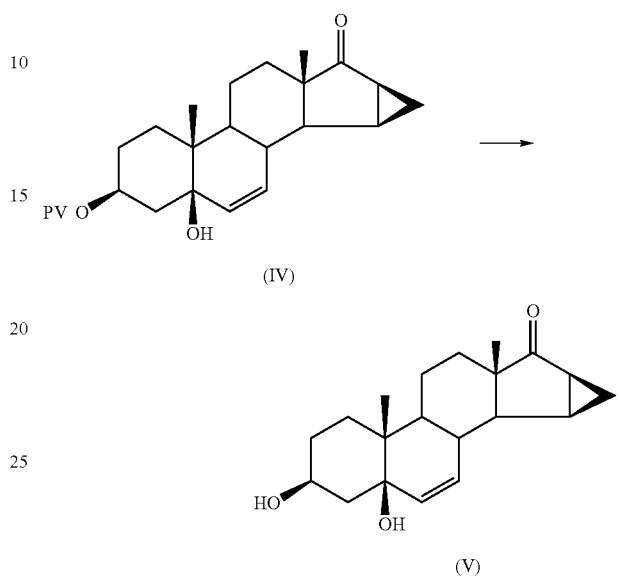

in which PV is defined as above, d) methylenation at the $\Delta^6$ double bond of 3β,5-dihydroxy-15β,16β-methylene-5β-androst-6-en-17-one of formula (V) coming from step c), to obtain 3β,5-dihydroxy-6β,7β; 15β,16β-dimethylene-5β-androst-17-one of formula (VI)

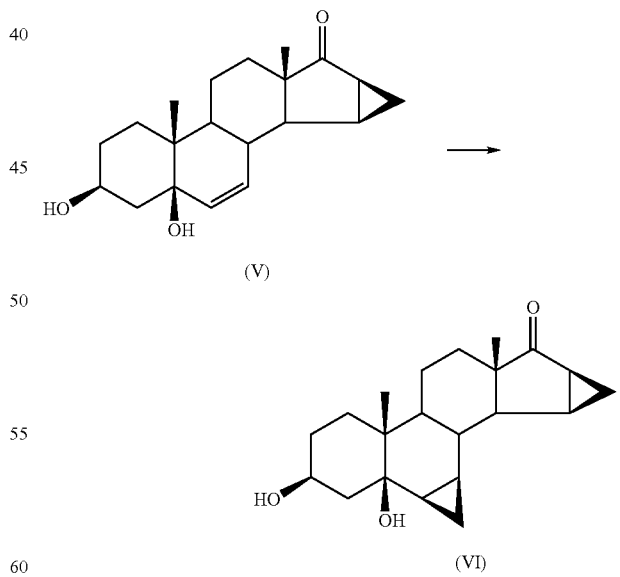

e) reacting 3β,5-dihydroxy-6β,7β; 15β,16β-dimethylene-5β-androst-17-one of formula (VI) coming from step d) with propargyl alcohol to obtain 17α-(3-hydroxy-1-propinyl)-6β,7β; 15β,16β-dimethylene-5β-androstane-3β,5,17β-triol of formula (VII)

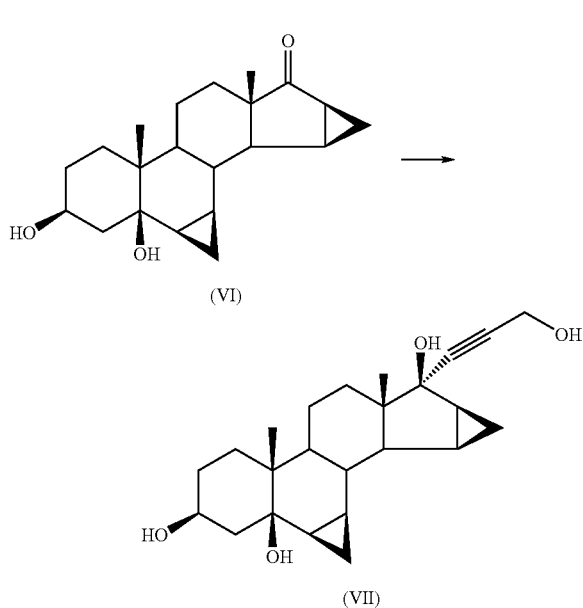

(VI)

(VII)

f) hydrogenating 17α-(3-hydroxy-1-propinyl)-6β,7β; 15β, 16β-dimethylene-5β-androstane-3β,5,17β-triol of formula (VII) coming from step e) to obtain 17α-(3-hydroxypropyl)-6β,7β; 15β,16β-dimethylene-5β-androstane-3β, 5,17β-triol of formula (VIII)

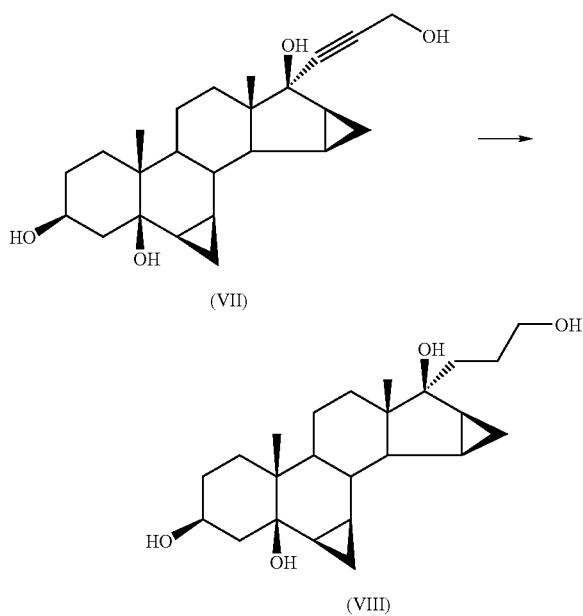

(VII)

(VIII)

The starting 5,6β-epoxy-7β-hydroxy-15β,16β-methylene-3β-pivaloyloxy-5β-androstan-17-one of formula (I) can be in its turn obtained from 3β-hydroxy-5-androsten-17-one as described in European Patent No. 0 075 189.

The bromination reaction in step a) is preferably carried out by adding mesyl chloride and pyridine to the starting compound at room temperature with the formation of the corresponding mesylate, then adding lithium bromide dissolved in water and bringing the temperature to values between 70 and 75° C.

The successive steps a) to f) can be carried out in accordance with procedures commonly utilised and known to any skilled person.

The term "suitable oxidising agent" in accordance with the invention means a product chosen from the group consisting of hypohalides of alkali and alkaline-earth metals, preferably calcium and sodium hypochlorite, iodine, oxygen in the presence of CuCl, potassium peroxymonosulfate $KHSO_5$ known commercially as Oxone®, and 1,3,5-trichloro-2,4,6-triazinetrione.

Derivatives of the 2,2,6,6-tetramethylpiperidine-1-oxyl radical of possible use in the present process are chosen for example from the 4-hydroxy-2,2,6,6-tetramethylpiperidine-1-oxyl radical, the 4-methoxy-2,2,6,6-tetramethylpiperidine-1-oxyl radical and the 4-(benzoyloxy)-2,2,6,6-tetramethylpiperidine-1-oxyl radical. As organic solvent for the oxidation reaction a solvent chosen from the group consisting of ethers such as acetone, methyl t-butyl ether and tetrahydrofuran, esters such as ethyl acetate, hydrocarbons such as toluene, halogenated hydrocarbons, such as methylene chloride, and mixtures thereof, can be used. The oxidation reaction and subsequent dehydration can be carried out for example at a temperature between 0 and 40° C., preferably at a temperature between 20 and 25° C.

Preferred reaction conditions are those in which the oxidation is carried out with calcium hypochlorite using as organic solvent a methylene chloride/tetrahydrofuran mixture, preferably in a 8.5/1 ratio, at a temperature between 20 and 25° C. in the presence of a catalytic amount of 2,2,6,6-tetramethylpiperidine-1-oxyl radical and in the presence of an aqueous sodium bicarbonate solution.

At the end of the oxidation reaction a protic acid is added directly to the organic solution in which the oxidation reaction took place. Alternatively, the organic solution in which the oxidation reaction took place is distilled until a semi-solid residue is obtained which is then redissolved in a suitable organic solvent, and to the so obtained solution the protic acid is then added.

The aforesaid protic acid is chosen for example from the group consisting of concentrated hydrochloric acid, dilute hydrochloric acid and p-toluenesulfonic acid; preferably the protic acid used is p-toluenesulfonic acid monohydrate.

The crude drospirenone obtained with the present process as described above has a high degree of purity, being greater than 96.5%, which can nevertheless be increased by subjecting the crude product coming from the oxidation to a purification procedure to obtain drospirenone with a degree of purity greater than 99.5%.

To obtain drospirenone with said degree of purity no chromatographic procedure is necessary, but a filtration through gel and decolourising carbon is sufficient, followed by crystallisation of the filtrate from solvent, the two steps of filtration and crystallisation possibly being repeated one or more times.

Preferably the gel utilised in accordance with the invention is silica gel, while the crystallisation solvent can be chosen from the group consisting of ethyl ether, isopropyl ether, ethyl acetate, methyl tertbutyl ether, isopropyl acetate, methyl acetate, dimethoxyethane, methanol, ethanol, isopropanol, methylene chloride, acetone, dimethylacetamide, dimethylformamide and mixtures thereof; the preferred crystallisation solvent is isopropyl acetate.

In accordance with a particularly preferred embodiment of the invention, the present purification procedure comprises the following steps:

i) dissolving crude drospirenone in a suitable organic solvent, further containing silica gel and decolourising carbon, and filtering the solution thus obtained;
ii) distilling the solution coming from step i) and redissolving the distillate in a second organic solvent;
iii) distilling the solution coming from step ii) and redissolving the distillate in said second organic solvent;
iv) crystallising pure drospirenone from the solution coming from step iii);
v) recovering pure drospirenone by filtering, washing over the filter at least once with a suitable organic solvent, then drying at a pressure lower than atmospheric pressure;
vi) if necessary repeating steps i) to v), starting from the drospirenone coming from step v).

The amount of silica gel and decolourising carbon employed in step i) is preferably less than 5% by weight with respect of the weight of the crude drospirenone to be purified.

The distillation steps ii) and iii) are preferably carried out at a distillation temperature between 35 and 45° C., and at a pressure lower than atmospheric pressure.

In step iv) said crystallisation is carried out at a temperature between 0 and 5° C. for a time period between 60 and 180 minutes.

The organic solvent used in steps i), ii), iii) and v) is chosen for example from the group consisting of ethyl ether, isopropyl ether, ethyl acetate, isopropyl acetate, methyl acetate, dimethoxyethane, methanol, ethanol, isopropanol, methylene chloride, acetone, dimethylacetamide, dimethylformamide, methyl tertbutyl ether and mixtures thereof.

Preferably the organic solvent in step i) is methylene chloride, the organic solvent in step ii) is isopropyl acetate, and in step v) two washings are undertaken, the first with isopropyl acetate and the second with ethyl ether.

The present process for drospirenone preparation as described above has proved to be advantageous in that it enables preparation of the intermediate 7α-bromo-5,6β-epoxy-15β,16β-methylene-3β-pivaloyloxy-5β-androstan-17-one, useful for drospirenone synthesis, while avoiding toxic solvents and reagents such as tetrachloromethane as used in the process given in EP 0 075 189. Furthermore, though preparation of this brominated intermediate passes via the formation of a mesylated intermediate, it does not involve an additional process step because the mesylate is not isolated but brominated directly.

The use of carcinogenic reagents is also avoided in the oxidation step which, as well as not requiring carcinogenic reagents, is just as efficient as the oxidation with chromic anhydride described in EP 0 075 189.

Finally, the purification process described above enables the inverted lactone fraction that is present in the crude product and identified as ZK35096 in U.S. Pat. No. 6,121,465, to be completely eliminated without the use of chromatographic techniques. This purification process is applicable and useful for the purification not only of drospirenone prepared in accordance with the present process, but also of products obtained with other processes and in which the aforementioned inverted lactone is present as impurity.

The following examples are given as non-limiting illustrations of the present invention.

EXAMPLE 1

Preparation of 7α-bromo-5,6β-epoxy-15β,16β-methylene-3β-pivaloyloxy-5β-androstan-17-one—Step a 67.5 g of 5,6β-epoxy-7β-hydroxy-15β,16β-methylene-3β-pivaloyloxy-5β-androstan-17-one are dissolved in 205 ml of pyridine in a 2 litre flask, under nitrogen.

17.5 ml of mesyl chloride are added from a dropping funnel, maintaining a temperature of 20/25° C.

The mixture is stirred for 1 hour at 20° C. to obtain a thick orange suspension.

The progress of the reaction is checked by TLC. Once the reaction is completed, 83.2 g of lithium bromide dissolved in 54 ml of water are added and the temperature is brought to 70/75° C. After 3 hours another 8 g of lithium bromide dissolved in water and 50 ml of pyridine are added.

At the end of the reaction (checked by TLC) the temperature is brought to 60° C. and 700 ml of water are added; it is left to cool to 15/20° C., maintaining under stirring for 1 hour at this temperature.

The solid is filtered off and washed with 500 ml of water.

The solid is dried for 24 hours under reduced pressure at 45° C. to obtain 69.5 g of the title compound.

On the product thus obtained, purified by chromatography, $^1$H-NMR and mass spectroscopic analyses were carried out, and the following results were obtained:

$^1$H-NMR (300 MHz, CDCl$_3$): δ (ppm) 0.92 (18-Me, s, 3H); 1.04 (19-Me, s, 3H); 1.08-1.16 (m, 1H); 1.16 (t-But, s, 9H); 1.18-1.28 (m, 1H); 1.36-1.60 (m, 8H); 1.62-1.68 (m, 1H); 1.72-1.76 (m, 1H); 1.84-1.96 (m, 3H); 2.04-2.16 (m, 3H); 3.46 (6-H, broad s, 1H); 4.73 (7-H, broad s, 1H); 4.76-4.84 (3-H, m, 1H).

Electron impact mass spectroscopy: m/z [376] and [378]= M$^+$-C(CH$_3$)$_3$—COOH; [297] and [299]=M$^+$-C(CH$_3$)$_3$—COOH—Br

EXAMPLE 2

Preparation of 5-hydroxy-15β,16β-methylene-3β-pivaloyloxy-5β-androst-6-en-17-one—Step b 27 g of powdered zinc suspended in 91 ml of THF (tetrahydrofuran) are fed into a 1 litre flask, under nitrogen.

A solution of 67.5 g of 7α-bromo-5,6β-epoxy-15β,16β-methylene-3β-pivaloyloxy-5β-androstan-17-one, prepared as described in Example 1, in 277 ml of THF is then added; 19.9 ml of glacial acetic acid are slowly added dropwise, maintaining the temperature below 60° C. during the addition. The reaction mixture is maintained under stirring for 3 hours at 59/60° C.

At the end of the reaction (checked by TLC) and after cooling to 50° C., the zinc is filtered off over dicalite and the filter washed with 200 ml of THF.

The filtered solution is brought to pH 9 with 60 ml of triethylamine.

The solution is concentrated under reduced pressure at 50° C. to obtain about 180 g of a semi-solid product which is dissolved in 500 ml of a 5% acetic acid-water solution (pH=4 with a precipitate).

It is maintained under stirring for 1 hour at 10/15° C., the solid is filtered off and washed with 500 ml of water then dried under reduced pressure for 12 hours at 50° C., thus obtaining 57 g of crude product.

The crude product is refluxed for 1 hour in a mixture of 115 ml of t-butyl methyl ether and 114 ml of ethyl acetate (partial dissolution).

It is cooled for 1 hour at 0/5° C., the solid is filtered off and washed with t-butyl methyl ether and dried under reduced pressure for 1 hour at 60° C. 44.6 g of the title compound are obtained.

The analytical data obtained from a sample purified by chromatography correspond to those given in EP 0 075 189.

EXAMPLE 3

Preparation of 3β,5-dihydroxy-15β,16β-methylene-5β-androst-6-en-17-one—Step c 43 g of 5-hydroxy-15β,16β-methylene-3β-pivaloyloxy-5β-androst-6-en-17-one prepared as described above in Example 2, 430 ml of THF, 215 ml of methanol and 12.9 g of potassium hydroxide are fed into a 2 litre flask, under nitrogen at 20° C. The suspension is stirred at 20° C. for 3 hours.

At the end of the reaction (checked by TLC), the reaction mixture is poured into 2 litres of water, brought to pH 7 with 20% sulphuric acid (about 25 ml) then the suspension is stirred for 1 hour at 0/5° C. The solid is filtered off, washed with water and dried for 12 hours under reduced pressure at 50° C. to obtain 30.6 g of the title compound.

The analytical data obtained for a sample purified by chromatography correspond to those given in EP 0 075 189.

EXAMPLE 4

Preparation of 3β,5-dihydroxy-6β,7β; 15β,16β-dimethylene-5β-androst-17-one—Step d 29 g of 3β,5-dihydroxy-15β,16β-methylene-5β-androst-6-en-17-one prepared as described above in Example 3 are fed into a 2 litre flask under nitrogen at 20° C. with 410 ml of THF.

0.6 g of copper (II) acetate hydrate are added and the mixture is maintained under stirring until the solution is clear (green).

37.9 g of finely powered zinc are added and, after stirring for 15 minutes, 1.7 ml of acetic acid are further added.

The mixture is further stirred for 30 minutes at 20° C. then heated to 50° C.; 32.3 ml of methylene bromide are added and it is refluxed for 2 hours.

At the end of the reaction (checked by TLC) it is cooled to 20° C. and a mixture consisting of 26.8 ml acetic acid in 450 ml water is added slowly while cooling.

The mixture is filtered through dicalite and the panel is washed with 600 ml of toluene.

The phases are separated and the aqueous phase is extracted with 200 ml of toluene. The joined organic phases are washed with 350 ml of water.

The organic phase is dried over sodium sulphate, filtered and concentrated under reduced pressure at 60° C. until a solid is obtained.

The solid is dissolved with 50 ml of a 3/1 heptane/ethyl acetate mixture and filtered off, then dried for 12 hours under reduced pressure at 45° C. to obtain 25.5 g of the title compound.

The analytical data obtained from a sample purified by chromatography correspond to those given in EP 0 075 189.

EXAMPLE 5

Preparation of 17α-(3-hydroxy-1-propinyl)-6β,7β; 15β,16β-dimethylene-5β-androstane-3β,5,17β-triol—Step e 24 g of 3β,5-dihydroxy-6β,7β; 15β,16β-dimethylene-5β-androst-17-one prepared as described above in Example 4 are fed into a 1 litre flask, under nitrogen at 20° C., with 480 ml of THF.

The mixture is cooled to 0/5° C. and 72 g of potassium methylate are added (yellow suspension).

While maintaining the temperature at 0/5° C. 48 ml of propargyl alcohol diluted with 90 ml of THF are added slowly (thick orange solution).

A further 150 ml of THF are added when the solution density renders stirring impossible. The solution is maintained under stirring for 12 hours at 0/5° C.

At the end of the reaction (checked by TLC) the very thick suspension is poured into 2 litres of water and ice (an orange solid precipitates).

The solid obtained is extracted with 1.5 litres of isopropyl acetate.

The organic phase is dried over sodium sulphate, filtered and concentrated under reduced pressure at 50° C. to obtain a solid.

The solid is filtered off from heptane and dried for 12 hours at 45° C. under reduced pressure to obtain 27.1 g of the title compound.

The analytical data obtained from a sample purified by chromatography correspond to those given in EP 0 075 189.

EXAMPLE 6

Preparation of 17α-(3-hydroxypropyl)-6β,7β; 15β,16β-dimethylene-5β-androstane-3β,5,17β-triol—Step f A solution of 25.1 g 17α-(3-hydroxy-1-propinyl)-6β,7β; 15β,16β-dimethylene-5β-androstane-3β,5,17β-triol prepared as described above in Example 5, in 930 ml of a mixture prepared with 750 ml of THF, 375 ml of methanol and 1.5 ml of pyridine is fed into an autoclave.

5 g of 5% Pd/C catalyst are added and hydrogenation is carried out at atmospheric pressure (20/25° C.) for 2 hours.

At the end of the reaction (checked by TLC) the suspension is filtered through dicalite then the filter is washed with methylene chloride.

The product is concentrated under reduced pressure at 50° C. to obtain 32 g of the title compound.

The crude title product contained small quantities of the two 6β,7β; 15β,16β-dimethylene-3β,5β-dihydroxy-17α-pregn-21,17-carbolactols. It was nevertheless advantageously used for the subsequent reaction, without any further purification. A sample of the title product purified by chromatography gave the following results with $^1$H-NMR analysis:

$^1$H-NMR (300 MHz, CDCl$_3$): δ (ppm) 0.84 (18-Me, s, 3H); 0.88 (19-Me, s, 3H); 1.72 (s, —OH); 2.32-2.40 (m, —OH); 2.6 (s, —OH); 3.38-3.40 (m, —OH); 3.64-3.76 (—CH$_2$OH, m, 2H); 4.0 (3-H, m, 1H).

The signals of the hydroxyl protons were identified by deuteration.

The crude reaction product used for the subsequent reaction also presented the following signals:

$^1$H-NMR (300 MHz, CDCl$_3$): δ (ppm) 5.50 (17-O—CHOH-21, t, 1H); 5.58 (17-O—CHOH-21, t, 1H).

EXAMPLE 7

Preparation of 6β,7β; 15β,16β-dimethylene-3-oxo-17α-pregn-4-en-21,17-carbolactone (DROSPIRENONE)—Oxidation 50 g of 17α-(3-hydroxypropyl)-6β,7β; 15β,16β-dimethylene-5β-androstane-3β,5,17β-triol prepared as described above in Example 6, 850 ml of methylene chloride and 100 ml of THF are fed into a reactor, and stirred at a temperature of 20° C.

A solution, prepared by dissolving 75 g of sodium bicarbonate in 750 ml of water, is added to the organic solution thus obtained.

While maintaining the biphasic solution under vigorous stirring at 20° C., 1.2 g of 2,2,6,6-tetramethylpiperidine-1-oxyl radical (TEMPO) and 35 g of calcium hypochlorite are added in portions, while monitoring oxidation reaction progress by TLC.

The biphasic solution is filtered, the two phases are left to separate, and the organic phase is washed first with an aqueous sodium bisulfate monohydrate solution then with water.

The organic phase is concentrated at 40° C. under vacuum until a semi-solid residue is obtained, which is then dissolved with 560 ml THF; 4.9 g of p-toluenesulfonic acid monohydrate are added to the solution thus obtained and maintained under stirring for 1 hour at 20° C., while monitoring the formation of drospirenone by means of TLC.

Once the reaction is completed the product is neutralised with an aqueous 10% sodium bicarbonate solution and extracted with 800 ml of isopropyl acetate. The organic phase is washed with water and concentrated under vacuum at 40° C.

The residue is firstly dissolved with isopropyl acetate then concentrated again under vacuum at 40° C. and dissolved once more with isopropyl acetate at 0/5° C., to obtain a suspension.

By filtering this suspension, washing the solid with ethyl ether and drying it under vacuum at 40° C., 31.3 g of crude drospirenone are obtained which are then fed into a container with 150 ml of methylene chloride. 2 g of decolourising carbon and 1.45 g of silica gel are then added. The suspension is then filtered and concentrated to a small volume by distillation under vacuum at 40° C.

The residue is then dissolved with isopropyl acetate, concentrated to a small volume by distillation under vacuum at 40° C., again dissolved with 25 ml of isopropyl acetate and maintained under stirring at 30° C. for 15 minutes, then at 0/2° C. for 2 hours.

After filtering, the solid obtained is washed first with cold isopropyl acetate then with ethyl ether. After drying under vacuum at 40° C. until a constant weight is achieved, 28.9 g of drospirenone are obtained whose analytical data correspond with those given in the literature.

EXAMPLE 8

Preparation of 6β,7β; 15β,16β-dimethylene-3-oxo-17α-pregn-4-en-21,17-carbolactone (DROSPIRENONE)—Oxidation 12 g of 17α-(3-hydroxypropyl)-6β,7β,15β,16β-dimethylene-5β-androstane-3β,5,17β-triol prepared as described above in Example 6, 170 ml of methylene chloride and 20 ml of THF are fed into a reactor. The mixture is stirred at 20° C. until a homogeneous solution is obtained.

A solution, prepared by dissolving 15 g of sodium bicarbonate in 150 ml of water, is added to the organic solution thus obtained.

While maintaining the biphasic solution under vigorous stirring at 20° C., 0.54 g of 2,2,6,6-tetramethylpiperidine-1-oxyl radical (TEMPO) and 8.6 g of calcium hypochlorite are added in portions, while monitoring oxidation reaction progress by TLC.

On completion of the oxidation, the biphasic solution is filtered and the two phases are left to separate. 1.5 g of p-toluenesulfonic acid monohydrate are added to the organic phase.

The mixture is maintained under stirring for about 3 hours at 20° C., while monitoring the reaction by TLC.

When the reaction is complete, neutralisation is carried out with an 1% aqueous sodium bicarbonate solution.

The reaction proceeds as described above in Example 7 to finally obtain 6.5 g of drospirenone whose analytical data correspond to those given in the literature and those obtained for the product in Example 7.

The invention claimed is:

1. Process for the preparation of drospirenone, comprising the oxidation of 17α-(3-hydroxypropyl)-6β,7β,15β,16β-dimethylene-5β-androstane-3β,5,17β-triol of formula (VIII) with a suitable oxidising agent in an organic solvent in the presence of a catalytic amount of the 2,2,6,6-tetramethylpiperidine-1-oxyl radical or a derivative thereof, said oxidation being followed by the addition of a protic acid directly into the same container in which the oxidation took place, to obtain the drospirenone of formula (I)

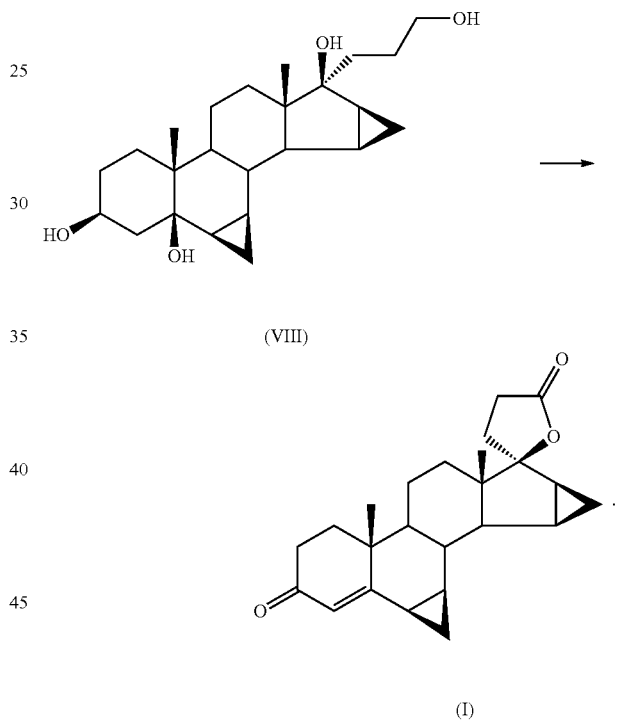

2. The process according to claim 1, wherein said 17β-(3-hydroxypropyl) -6β,7β,15β,16β-dimethylene-5β-androstane-3β,5,17β-triol of formula (VIII) is prepared starting from 5,6β-epoxy-7β-hydroxy-15β,16β-methylene-3β-pivaloyloxy-5β-androstan-17-one of formula (II) in accordance with the following steps:

a) bromination in position 7α of 5,6 β-epoxy-7β-hydroxy-15β,16β-methylene-3β-pivaloyloxy-5β-androstan-17-one of formula (II) to obtain 7α-bromo-5,6β-epoxy-15β,16β-methylene-3β-pivaloyloxy-5β-androstan -17-one of formula (III) by reacting the compound of formula (II) with mesyl chloride to obtain the corresponding mesylate which is not isolated and from which the compound of formula (III) is obtained by adding lithium bromide:

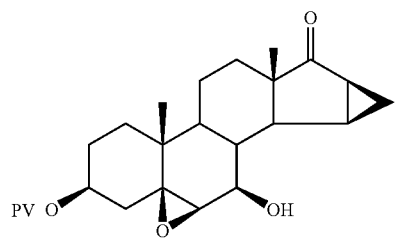

(II)

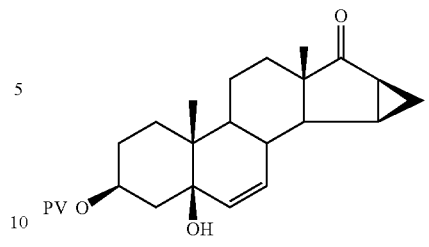

(IV)

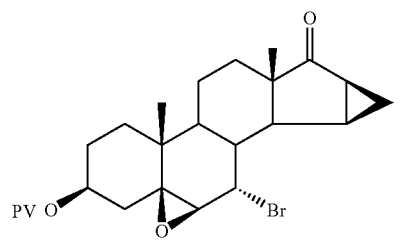

(III)

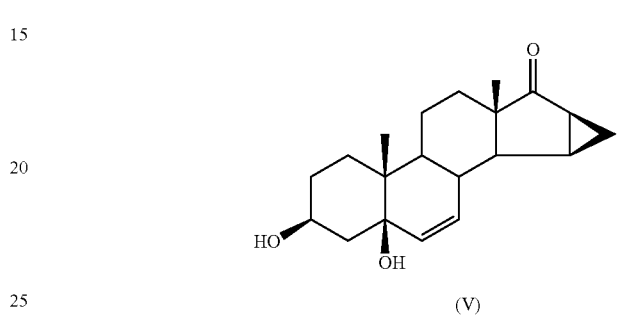

(V)

in which the symbol PV indicates a pivaloyl group, i.e. a trimethylacetyl group;

b) opening the epoxy ring and removing the bromine from 7α-bromo-5,6β-epoxy-15β,16β-methylene-3β-pivaloyloxy-5β-androstan-17-one of formula (III) derived from step a) to obtain the 5-hydroxy-15β,16β-methylene-3β-pivaloyloxy-5β-androst-6-en-17-one of formula (IV):

in which PV is defined as above, d) methylenation at the Δ$^6$ double bond of 3β,5-dihydroxy-15β,16β-methylene-5β-androst-6-en-17-one of formula (V) coming from step c) to obtain the 3β,5-dihydroxy-6β,7β;15β,16β-dimethylene-5β-androst-17-one of formula (VI)

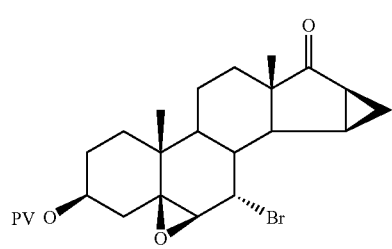

(III)

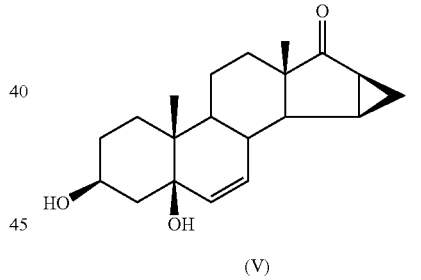

(V)

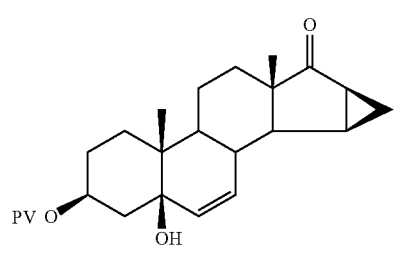

(IV)

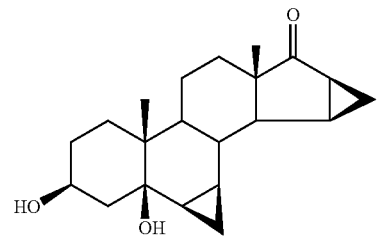

(VI)

c) hydrolysis of the pivaloyl group of 5-hydroxy-15β,16β-methylene-3β-pivaloyloxy -5β-androst-6-en-17-one of formula (IV) coming from step b) to obtain the 3β,5-dihydroxy-15β,16β-methylene-5β-androst-6-en-17-one of formula (V):

e) reacting the 3β,5-dihydroxy- 6β,7β;15β,16β-dimethylene-5β-androst-17-one of formula (VI) coming from step d) with propargyl alcohol to obtain the 17β-(3-hydroxy-1-propinyl)-6β,7β;15β,16β-dimethylene-5β-androstane-3β,5, 17β-triol of formula

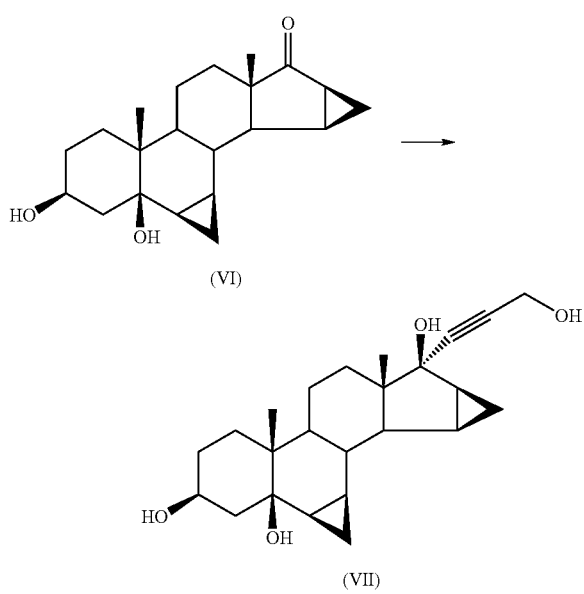

(VI)

(VII)

f) hydrogenating the 17α-(3-hydroxy-1-propinyl)-6β,7β;15β,16β-dimethylene-5β-androstane-3β,5,17β-triol of formula (VII) coming from step e) to obtain the 17α-(3-hydroxypropyl)-6β,7β;15β,16β-dimethylene-5β-androstane-3β,5,17β-triol of formula (VIII)

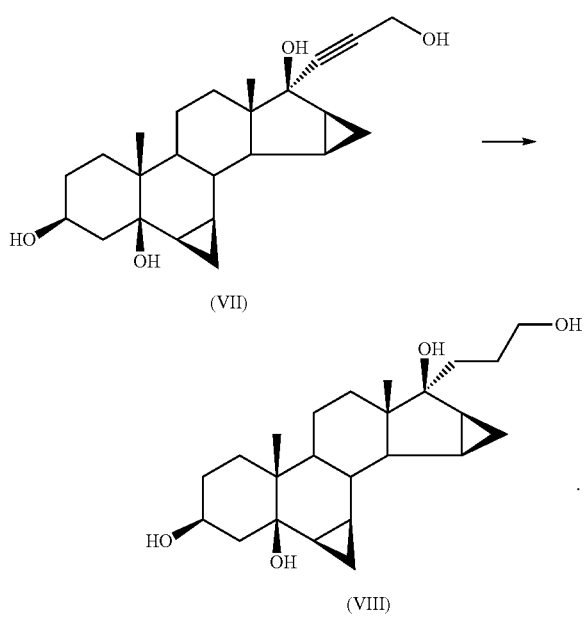

(VII)

(VIII)

3. The process according to claim 1, wherein said oxidising agent is selected from the group consisting of alkali metal and alkaline-earth metal hypohalides, iodine, oxygen in the presence of CuCl, potassium peroxymonosulphate and 1,3,5-trichloro-2,4,6-triazinetrione.

4. The process according to claim 3, wherein said oxidising agent is selected from sodium hypochlorite and calcium hypochlorite.

5. The process according to claim 1, wherein said derivative of the 2,2,6,6-tetramethylpiperidine-1-oxyl radical is selected from the group consisting of the 4-hydroxy-2,2,6,6-tetramethylpiperidine-1-oxyl radical, the 4-methoxy-2,2,6,6-tetramethylpiperidine-1-oxyl radical and the 4-(benzoyloxy)-2,2,6,6-tetramethylpiperidine-1-oxyl radical.

6. The process according to claim 1, wherein said organic solvent is selected from the group consisting of ethers, esters, hydrocarbons, halogenated hydrocarbons and mixtures thereof.

7. The process according to claim 1, wherein said organic solvent is selected from the group consisting of acetone, toluene, methyl t-butyl ether, ethyl acetate, methylene chloride, tetrahydrofuran and mixtures thereof.

8. The process according to claim 1, wherein said oxidation is carried out at a temperature between 0 and 40° C.

9. The process according to claim 1, wherein said oxidation is carried out with calcium hypochlorite using as organic solvent a methylene chloride/tetrahydrofuran mixture at a temperature between 20 and 25° C. in the presence of a catalytic amount of the 2,2,6,6-tetramethylpiperidine-1-oxyl radical and in the presence of an aqueous sodium bicarbonate solution.

10. The process according to claim 9, wherein said methylene chloride/tetrahydrofuran mixture is used in a ratio of 8.5/1.

11. The process according to claim 1, wherein said protic acid is selected from the group consisting of concentrated hydrochloric acid, dilute hydrochloric acid and p-toluenesulfonic acid.

12. The process according to claim 11, wherein said protic acid is p-toluenesulfonic acid monohydrate.

13. The process according to claim 1, wherein said protic acid addition is carried out at a temperature between 0 and 40° C.

14. The process according to claim 13, wherein said protic acid addition is carried out at a temperature between 20 and 25° C.

15. The process according to claim 1, wherein said protic acid is added directly to the organic solution in which the oxidation reaction took place.

16. The process according to claim 1, wherein the organic solution in which the oxidation reaction took place is distilled until a residue is obtained, said residue is redissolved in a suitable organic solvent, and said protic acid is then added to the so-obtained solution.

17. The process according to claim 2, wherein said bromination reaction in step a) is carried out by adding mesyl chloride and pyridine to the starting compound at room temperature with the formation of the corresponding mesylate, then adding lithium bromide dissolved in water and bringing the temperature to values between 70 and 75° C.

18. The process according to claim 1, further comprising purification of the crude drospirenone by a procedure comprising gel filtration and filtrate crystallisation from organic solvent, said procedure possibly being repeated one or more times.

19. The process according to claim 18, wherein said purification comprises the following steps:
i) dissolving crude drospirenone in a suitable organic solvent, further containing silica gel and decolourising carbon, and filtering the solution thus obtained;
ii) distilling the solution coming from step i) and redissolving the distillate in a second organic solvent;
iii) distilling the solution coming from step ii) and redissolving the distillate in said second organic solvent;
iv) crystallising pure drospirenone from the solution coming from step iii);

v) recovering pure drospirenone by filtering, washing over the filter at least once with a suitable organic solvent, and drying at a pressure lower than atmospheric pressure;

vi) optionally repeating steps i) to v), starting from the drospirenone coming from step v).

20. The process according to claim 19, wherein the amount of silica gel and decolourising carbon utilised is less than 5% by weight with respect to the weight of the crude drospirenone to be purified.

21. The process according to claim 19, wherein the distillation temperature in steps ii) and iii) is between 35 and 45° C.

22. The process according to claim 19, wherein said distillation in steps ii) and iii) is carried out at a pressure lower than atmospheric pressure.

23. The process according to claim 19, wherein said crystallisation in step iv) is carried out at a temperature between 0 and 5° C. for a time period between 60 and 180 minutes.

24. The process according to claim 19, wherein said organic solvent in steps i), ii), iii) and v) is selected from the group consisting of ethyl ether, isopropyl ether, ethyl acetate, methyl tertbutyl ether, isopropyl acetate, methyl acetate, dimethoxyethane, methanol, ethanol, isopropanol, methylene chloride, acetone, dimethylacetamide, dimethylformamide and mixtures thereof.

25. The process according to claim 19, wherein said organic solvent in step i) is methylene chloride, said organic solvent in step ii) is isopropyl acetate, and in step v) two washings are carried out, the first with isopropyl acetate and the second with ethyl ether.

* * * * *